United States Patent [19]

Matsumoto et al.

[11] Patent Number: 4,588,836

[45] Date of Patent: May 13, 1986

[54] NOVEL SYNTHETIC SUBSTRATE AND ASSAY METHOD USING THE SAME

[75] Inventors: Kunio Matsumoto; Yoshitaka Kagimoto; Tsutomu Hirata; Susumu Watanabe, all of Shizuoka; Akira Ohtsuka, Kanagawa; Kiyoharu Takahashi, Saitama, all of Japan

[73] Assignees: Toyo Jozo Kabushiki Kaisha, Shizuoka; Kokusan Chemical Works Limited, Tokyo, both of Japan

[21] Appl. No.: 526,031

[22] Filed: Aug. 24, 1983

[30] Foreign Application Priority Data

Sep. 1, 1982 [JP] Japan .................................. 57-150701
Nov. 15, 1982 [JP] Japan .................................. 57-198862

[51] Int. Cl.4 .......................... C07C 101/72; C12Q 1/48
[52] U.S. Cl. ..................................... 562/448; 564/194; 435/15; 435/25
[58] Field of Search ................ 564/194; 562/448, 449, 562/450; 560/39

[56] References Cited

U.S. PATENT DOCUMENTS

| | | | |
|---|---|---|---|
| 2,873,294 | 2/1959 | Kline | 562/448 |
| 3,442,892 | 5/1969 | Kusuda et al. | 564/194 |
| 3,542,850 | 11/1970 | Jansen et al. | 564/194 |
| 3,903,147 | 9/1975 | Kyncl et al. | 564/448 |
| 4,031,242 | 6/1977 | Jones et al. | 560/39 |
| 4,177,109 | 12/1979 | Tohyama et al. | 562/450 |
| 4,209,459 | 6/1980 | Nagasawa et al. | 562/451 |

FOREIGN PATENT DOCUMENTS 2103607  2/1983  United Kingdom ................. 435/25

*Primary Examiner*—James H. Reamer
*Attorney, Agent, or Firm*—Ladas & Parry

[57] ABSTRACT

A compound of the formula

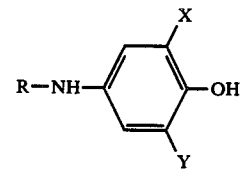

wherein R is L-leucyl or γ-L-glutamyl and X and Y are halogen and are the same or different, or a salt thereof. These compounds are useful as synthetic substrates for assaying peptidase activity.

7 Claims, 20 Drawing Figures

NOVEL SYNTHETIC SUBSTRATE AND ASSAY METHOD USING THE SAME

BACKGROUND OF THE INVENTION

This invention relates to a novel synthetic substrate for assaying peptidase activity and an assay method of peptidase. More particularly, the present invention relates to an amide compound of the formula

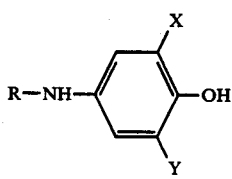

wherein R is L-leucyl or γ-L-glutamyl and X and Y are the same or different, and are halogen atom or salt thereof, and an assay method of peptidase which comprises:

An assay method of enzyme activity which comprises treating an amide compound of the formula

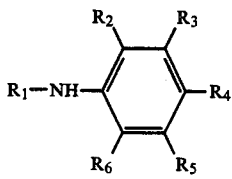

wherein $R_1$ is L-leucyl or γ-L-glutamyl group, $R_2$, $R_3$, $R_4$, $R_5$ and $R_6$ are hydrogen, halogen, lower alkyl, lower alkoxy, amino, substituted amino, hydroxyl, carboxyl or sulfo group and $R_5$ and $R_6$ in together may be constituted the carbon ring, or water soluble salt thereof with peptidase, treating the thus liberated amine of the formula

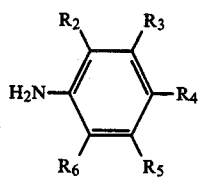

wherein $R_2$, $R_3$, $R_4$, $R_5$ and $R_6$ have the same meanings hereinabove, with oxidase which consumes oxygen and forms pigment in the presence of a coupler of the formula

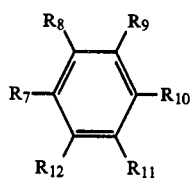

wherein $R_7$ is hydrogen, amino, substituted amino or hydroxyl group, $R_8$, $R_9$, $R_{10}$, $R_{11}$ and $R_{12}$ are hydrogen, halogen, lower alkyl, lower alkoxy, amino, substituted amino, hydroxyl, carboxyl or sulfo group, and $R_{11}$ and $R_{12}$, in together, may optionally be carbon ring, or $R_7$ may optionally be hydrogen when at least one of $R_8$, $R_9$, $R_{10}$, $R_{11}$ and $R_{12}$ is amino, substituted amino or hydroxyl, then quantitatively measuring the detectable changes, and an assay method which comprises treating an amide compound of the formula

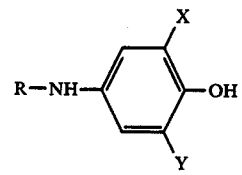

wherein R is L-leucyl or γ-L-glutamyl group, and X and Y are the same or different and are halogen atom, or salt thereof, with peptidase in a sample to liberate aniline derivative of the formula

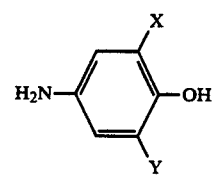

wherein X and Y have the same meanings hereinbefore, oxidizing the said aniline derivative, and quantitatively measuring the detectable Peptidase has been known as a general term for enzyme which acts on peptide bond in L-peptide and splitting at N-terminal to liberate amino acids or lower peptides. For example, aminopeptidase such as leucine aminopeptidase (True LAP in clinical chemistry) or arylamidase (Clinical LAP in clinical chemistry, hereinafter sometimes designates AA)(hereinafter True LAP and Clinical LAP are generically designates as LAP), cystine aminopeptidase, proline aminopeptidase, arginine aminopeptidase, alanine aminopeptidase or γ-glutamyl transpeptidase (γ-GTP) has been known.

Among the enzyme hereinabove, LAP and γ-GTP are widely distributed in the tissues in vivo, and in serum. These enzymes are increased in disease condition and are important marker for clinical diagnosis and important items for enzyme activity assay in clinical determination.

LAP is an enzyme which hydrolyses amino-terminal residue of L-peptide having L-leucine or peptide related thereto as N-terminal residue to liberate L-leucine, and is distributed in tissue in vivo and in serum. An amount of LAP in serum is varied depending upon the conditions of body, and is increased at acute hepatitis, hepatoma, metastatic hepatoma, hepatocirrhosis and cholangitis. Therefore, LAP activity is a marker of these symptoms, and assay of LAP activity is indispensable for clinical diagnosis of these symptoms.

γ-GTP is an enzyme relating to metabolism of γ-glutamylpeptide in vivo and catalyzes the reaction of hydrolyzing the γ-glutamyl group in γ-glutamyl peptides and transferring the said group to other amino acids or peptides, and is widely distributed in tissues in vivo and in serum. γ-GTP in serum varies depending on the conditions of symptoms. The clinical value of serum γ-GTP is said to be higher in cholestatic hepatitis, obstructive jaundice and primary metastatic hepatoma and active chronic hepatitis, and lower in non-active chronic hepatitis, The determination of serum γ-GTP activity is specific for chronic hepatitis and is useful for clinical diagnosis and pathological ascertainment of these diseases.

Heretofore assay method of LAP has been known, most of those are colorimetric assay method of liberated amine compound for LAP activity. In the assay, L-leucyl-p-nitroanilide is used as synthetic substrate and yellow color of p-nitroaniline generated by enzymatic action of LAP is measured, however at the colorimetric determination of the said color, color absorption maximum is disadvantageously overlapped, moreover serum component such as bilirubin pigment affects disadvantageously. Also, a method using synthetic substrate L-leucyl-β-naphthylamide has been known, however the said method has number of disadvantages. The assay method is quite complex and required precise performance, for example the formed β-naphthylamine is coupled with 5-nitro-2-aminomethoxybenzene diazotate to form pigment, or β-naphthylamine thus formed is diazotated with sodium nitrite to couple with N-(1-naphthyl)-ethylenediamine or is condensated with p-dimethylaminobenzaldehyde or p-dimethylamino cinnamaldehyde to form pigment which is colorimetrically assayed. Further, the standard substance, β-naphthylamine, is toxic for inducing carcinoma or tumor of bladder.

Assay methods of γ-GTP are known and most of them are colorimetric assay of a liberated amine compound from synthetic substrate by γ-GTP. For example an assay method using γ-glutamyl-p-nitroanilide is that γ-glutamyl-p-nitroanilide is treated with γ-GTP to liberate yellow-colored p-nitroaniline which is colorimetrically measured at 410 nm. The absorbancy at 410 nm is inhibited by compound in body fluids, especially bilirubin. In order to avoid the effect of bilirubin pigment, control assay for specimen should be strictly and exactly measured, which causes disadvantages. Also liberated p-nitroaniline is condensed with an aldehyde such as p-dimethylamino cinnamaldehyde or p-dimethylaminobenzaldehyde to produce a color which is colorimetrically assayed at long-wave length red color. This colorimetric assay procedure is affected by temperature for coloring sensitivity and so is troubles for reproducibility. Further, a method wherein the produced p-nitroaniline is diazotized and condensed with 3,5xylenol and the thus formed red color is measured, is provided. This assay method, however, is quite complex and required multi reaction steps. Furthermore, an assay method using synthetic substrate γ-L-glutamyl-β-naphthylamide is provided. In this method, liberated β-naphthylamine by γ-GTP is changed to the diazonium salt and is colorimetrically measured or is reacted with 3-methyl-2-benzothiazolinone hydrazone and oxidizing agent to produce color which is colorimetrically measured, or the aldehyde compound of coloring agent hereinbefore is condensed therewith to assay colorimetrically. In these methods, carcinogenicity of β-naphthylamine causes problem, and also these assay method requires strict control of complex reaction process which causes disadvantages.

We had previously found that amide compound of the formula (which does not exist in serum)

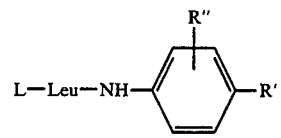

wherein R' is hydroxyl, amino or di-lower alkylamino and R" is hydrogen, lower alkyl or carboxyl, is excellent synthetic substrate for LAP and liberates amine compound by the action of LAP. The said amine compound is oxidized by the action of oxidase such as ascorbate oxidase or laccase and oxygen is consumed to form chromogen. LAP activity can be measured by measuring the amount of consumed oxygen or produced chromogen.

The assay method using the above synthetic substrate has disadvantages in which absorption maximum of chromogen is no more than 550 nm and is affected the contaminant in body fluid, and so is required the substrate which forms chromogen of higher absorption maximum.

SUMMARY OF THE INVENTION

We have found that amide compound of the formula [1] is superior synthetic substrate for LAP or γ-GTP, and the thus liberated amine compound is coupled with the coupler of the formula [3] by the action of oxidase with consuming oxygen to form chromogen, by oxidative condensation, which has higher absorption maxima at 550–750 nm and stable color tone. The said absorption is not affected by the contaminant in body fluid.

Further, we have found that a novel synthetic substrate, having the superior reactivity for assaying LAP or γ-GTP, of the following formula

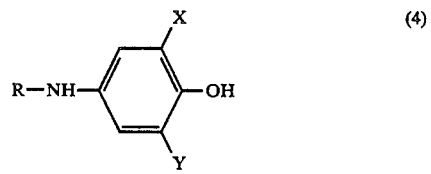
(4)

wherein R, X and Y have the same meanings hereinbefore, and amine compound of the formula

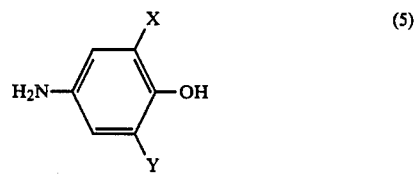
(5)

wherein X and Y have the same meanings hereinabove, is liberated from the above substrate by the action of LAP or γ-GTP, then is oxidized by oxidizing agent or oxidase to assay the enzyme activities.

An object of the present invention is to provide an assay method of enzyme activity which comprises treating an amide compound of the formula

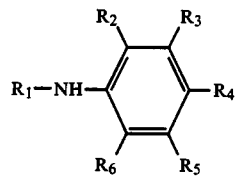

(1)

wherein $R_1$ is L-leucyl or $\gamma$-L-glutamyl group, $R_2$, $R_3$, $R_4$, $R_5$ and $R_6$ are hydrogen, halogen, lower alkyl, lower alkoxy, amino, substituted amino, hydroxyl, carboxyl or sulfo group and $R_5$ and $R_6$ in together may be constituted the carbon ring, or water soluble salt thereof with peptidase, treating the thus liberated amine of the formula

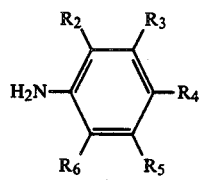

(2)

wherein $R_2$, $R_3$, $R_4$, $R_5$ and $R_6$ have the same meanings hereinabove, with oxidase which consumes oxygen and forms pigment in the presence of a coupler of the formula

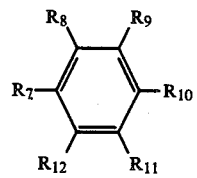

(3)

wherein $R_7$ is hydrogen, amino, substituted amino or hydroxyl group, $R_8$, $R_9$, $R_{10}$, $R_{11}$ and $R_{12}$ are hydrogen, halogen, lower alkyl, lower alkoxy, amino, substituted amino, hydroxyl, carboxyl or sulfo group, and $R_{11}$ and $R_{12}$, in together, may optionally be carbon ring, or $R_7$ may optionally be hydrogen when at least one of $R_8$, $R_9$, $R_{10}$, $R_{11}$ and $R_{12}$ is amino, substituted amino or hydroxyl, then quantitatively measuring the detectable changes.

Another object of the present invention is to provide an assay method which comprises treating an amide compound of the formula

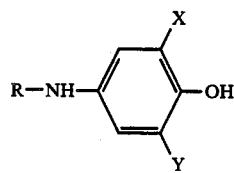

(4)

wherein R is L-leucyl or $\gamma$-L-glutamyl group, and X and Y are the same or different and are halogen atom, or salt thereof, with peptidase in a sample to liberate aniline derivative of the formula

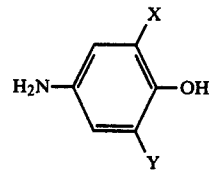

(5)

wherein X and Y have the same meanings hereinbefore, oxidizing the said aniline derivative, and quantitatively measuring the detectable changes.

Further object of the present invention is to provide a novel synthetic substrate for peptidase activity assay of the formula

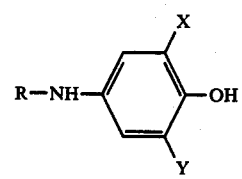

wherein R is L-leucyl or $\gamma$-L-glutamyl group and X and Y are the same or different, and are halogen atom, or salt thereof.

DESCRIPTION OF THE PREFERRED EMBODIMENTS

A synthetic substrate amide compound [1] or [4] for LAP or $\gamma$-GTP assay of the present invention can be produced by conventional methods of peptide synthesis, for example, by reacting the carboxyl group of L-leucine or $\gamma$-carboxyl group of L-glutamic acid with amine [2] or aniline derivative [5].

In the above condensation reaction, a reactive group for not taking part in the reaction, such as amino group of L-leucine or amino group and $\alpha$-carboxyl group of L-glutamic acid, should be protected. Example of protective group for amino group is conventional protective group for $\alpha$-amino group, such as t-butoxycarbonyl, t-amyloxycarbonyl, benzyloxycarbonyl, p-nitrobenzyloxycarbonyl or o-nitrophenylthio group. $\alpha$-carboxyl group of L-glutamic acid is preferably protected by methyl ester, ethyl ester, t-butyl ester, benzyl ester, p-nitrobenzyl ester or p-methoxybenzyl ester, and the said protective group can preferably be removed together with protective group for amino group in one step removal procedure. For example, amino group is protected by benzyloxycarbonyl, and $\alpha$-carboxyl group is protected by benzyl ester.

Examples of amine [2] used in the condensation reaction are lower alkyl, lower alkoxy, amino, substituted amino, hydroxy, carbonyl or sulfo group, for example o-(m- or p-) toluidine, o-(m- or p-) ethylaniline, 2,3-(2,4-, 2,5-, 2,6-, 3,4- or 3,5-) xylidine, o-(m- or p-) anisidine, 2,5-dimethoxyanilien, 2,5-diethoxyaniline, o-(m- or p-)chloroaniline, o-(m- or p-)bromoaniline, o (m- or p-)phenylenediamine, N,N-dimethyl-m-phenylenediamine, N,N-dimethyl-p-phenylenediamine, N,N-diethyl-p-phenylenediamine, N,N-dipropyl-p-phenylenediamine, o-(m- or p-)aminophenol, o-(m- or p-)aminobenzoic acid, p-aminobenzene sulfonic acid, 4-hydroxy-3,5-dichloroaniline, 4-hydroxy-3,5-dibromoaniline, 2-(or 4-)methyl-o-phenylenediamine, 2-hydroxy-5-toluidine, 3-(or 4-) chloro-o-toluidine, 2-(or 4-)methyl-m-phenylenediamine, 2-(or 4-) chloro-m-phenylenediamine, 4-methyl-m-aminobenzoic acid, 2-(or 3-) hydroxy-o-aminobenzoic acid, 4-hydroxy-m-aminobenzoic acid, 4-chloro-2-aminophenol, N-ethyl,N-hydroxyehtyl-p-phenylenediamine, 4-methyl-2-aminophenol, 2-methoxy-5-chloroaniline, 3-chloro-o-toluidine or 4-chloro-o-toluidine. Further example of amine [2] is naphthylamine compound, such as α-naphthylamine or 1-amino6-naphtholsulfonic acid.

Examples of aniline derivative [5] are 3,5-dibromo-4-hydroxyaniline, 3,5-dichloro-4-hydroxyaniline and 3-chloro-5-bromo-4-hydroxyaniline.

The condensation reaction is performed by that α-carboxyl group of L-leucine in which α-amino group is protected or γ-carboxyl group of L-glutamic acid in which α-amino and α-carboxyl group are protected, is activated by an acid halide, acid anhydride, acid azide, acid imidazolide or activated ester such as cyanomethyl ester, p-nitrophenyl ester, 2,4-dinitrophenyl ester, N-hydroxysuccineimide ester or N-hydroxyphthalimide ester and is reacted with amine [2] or aniline derivative [5]. Or the above protected L-leucine or L-glutamic acid is reacted with amine [2] or aniline [5] in the presence of condensing agent, for example carbodiimide such as N,N'-dicyclohexylcarbodiimide or N,N'-carbonylimidazole and isoxazolium salt such as Woodward reagent.

The above condensation reaction is carried out in an inert organic solvent such as dimethylformamide, dimethylacetamide, dimethylsulfoxide, tetrahydrofuran, dioxane, benzene, chloroform, dichloromethane or dichloroethane, with equal amount of protected amino acid and amine [2] or aniline derivative [5] at room temperature or below. The reaction process can be traced by silica gel thin layer chromatography (TLC) or high performance liquid chromatography (HPLC) and can be stopped upon checking the disappearance of starting material.

The thus obtained reaction product is dissolved, with or without distilling off the reaction solvent, in water immiscible organic solvent such as chloroform, dichloromethane, ethyl acetate, butyl acetate, methylisobutyl ketone, benzene or diethyl ether, washing with acidic water and alkaline water, and removing the sovent to isolate the product. If further purification is required, recrystallization is performed from suitable recrystallizing solvent or purification is made by silica gel, active alumina or adsorption resin column chromatography.

Removal of protective group can be made by conventional method of peptide chemistry. For example, t-butyloxycarbonyl group of α-amino group is removed by 2 N-HCl in acetic acid, trifluoroacetic acid or formic acid, and benzyloxycarbonyl is removed ny catalytic reduction using palladium carbon or HBr in acetic acid. Benzyl ester of α-carboxyl group of L-glutamic acid is removed by catalytic reduction using palladium-carbon.

The thus obtained amide compound [1] or amide compound [4] can be isolated by neutralizing the reaction mixture in case of acid decomposition removal of protective group or removing the catalyst in case of catalytic reduction, adding water immiscible organic solvent such as chloroform, dichloromethane, dichloroethane, ehtyl acetate, butyl acetate, methylisobutyl ketone, benzene or diethyl ether, washing with acidic water and alkaline water, and removing the solvent. Further pruification is made by recrystallization by suitable solvent or column chromatography using silicagel, active alumina or adsorption resin.

Amide compound [1] or amide compound [4] can optionally be prepared as salt thereof, for example, inorganic salt such as hydrochloride, sulfate, nitrate or phosphate, or organic salt such as formate, acetate, propionate, malate, citrate, tartrate or oxalate.

In the present invention, an amide compound [1] is hydrolysed by LAP or γ-GTP in sample to liberate amine [2] which is oxidatively condensed with coupler [3] by the action of oxidase to form chromogenic compound (hereinafter designates as chromogen) Examples of coupler [3] can be an aromatic compound which forms chromogen having absorption maxima at 550–750 nm and oxidatively condensed with amine [2] by the action of oxidase.

Preferable examples are phenols, aminophenols, anilines and naphthols. Examples of phenols are phenol, salicylic acid, m-hydroxybenzoic acid, p-hydroxybenzoic acid, 2,6-dihydroxybenzoic acid, methyl salicylate, o-(m- or p-)cresol, o-(or m-)ethylphenol, 2,3-(2,4-, 2,5-, 3,5- or 2,6-)xylenol, o-(m- or p-)methoxyphenol, 2,6-dimethoxyphenol, o-(m- or p-)chlorophenol, 2,4-( or 2,6-)dichlorophenol, o-(m- or p-)bromophenol, 2,4-(or 2,6-)dibromophenol, 2-methyl-6-chlorophenol, 2-chloro-5-methylphenol, o-carboxymethylphenol or 2-hydroxy-4-aminoethylphenol. Examples of aminophenols are 4-chloro-2-aminophenol, N,N-diethyl-m-aminophenol, 4-methyl2-aminophenol, 5-amino-2-hydroxybenzoic acid, 2-amino-3-hydroxybenzoic acid, o-(m- or p-)aminophenol, 2,6-dichloro-4-aminophenol or 2,6-dibromo-4-aminophenol. Examples of anilines are aniline, o-(m- or p-)toluidine, N-methylaniline, N-ethylaniline, N,N-dimethylaniline, N,N-diethylaniline, N,N-dimethyl-o-toluidine, N,N-dimethyl-p-toluidine, N,N-diethyl-o-toluidine, N,N-diethyl-p-toluidine, o-(or m-)chloroaniline, m-bromoaniline, anthranilic acid, 3-aminobenzoic acid, p-dimethylaminobenzoic acid, 4-chloro-o-toluidine, 3-aminoe-4-methylbenzoic acid, m-phenylenediamine, N,N-dimethyl-m-phenylenediamine, 4-methyl-o-phenylenediamine, 4-methyl-m-phenylenediamine, 2-chloro-m-phenylenediamine, 4-chloro-m-phenylenediamine, 3-chloro-o-toluidine, 2-methoxy-5-chloroaniline, o-ethylaniline, 2,5-diethoxyaniline, N-ethyl-N-hydroxyethylaniline or N-ethyl-N-hydroxyethyl-m-toluidine. Examples of naphthols are α-naphthol, β-naphthol, 1-naphthol-2carboxylic acid, 4-chloro-1-naphthol, 1-hydroxy-2-naphthoic acid, 1-naphthol-2-sulfonic acid, 1-naphthol-4-sulfonic acid, 1-naphthol-8-sulfonic acid, 2-naphthol-6-sulfonic acid, 2-naphthol7-sulfonic acid, 2-naphthol-8-sulfonic acid, 2-naphthol-3,6-disulfonic acid or 2-naphthol-6,8-disulfonic acid.

Examples of oxidase are oxidase which consumes oxygen and which can form chromogen by oxidizing the liberated amine [2] alone or by oxidatively coupling the liberated amine [2] with coupler [3]. For example, ascorbate oxidase, laccase, tyrosinase, aminophenol oxidase, phenol oxidase or polyphenol oxidase can be mentioned. Preferable examples are ascorbate oxidase obtained from pumpkin, cucumber or chayote (*Sechium edule*) [Japan. Unexam. Pat. Publ. No. 56-88793) or laccase obtained from japan (urushi, japanese lacquer) or Bacidiomycetes (*Coriolus versicolor*, Rhizopus or *Polyporus versicolor*) [J. Biochem., 50, 264 (1961), *Biochim. Biophys, Acta,* 73, 204 (1963), *Acta Chem. Scand.,* 21, 2367 1967)].

Embodiment of LAP or γ-GTP assay using amide compound [1] is as follows.

In the LAP assay, amide compound [1] of synthetic substrate for LAP, in which $R_1$ is L-leucyl group, or salt thereof is treated with LAP in sample (specimen) to liberate amine [2].

Sample is a specimen serum 0.01–5 ml. Enzyme reaction is carried out at 37° C. for 5 minutes or more. Optimum pH of the enzyme is pH 6.5–8.0. Example of buffer solution is phosphate, borate, barbital, carbonate or Tris hydroxymethylamino ethane buffer.

In the γ-GTP assay, amide compound [1] of synthetic substrate for γ-GTP, in which $R_1$ is γ-L-glutamyl group, or salt thereof is treated with γ-GTP in sample to liberate amine [2]. Amount of sample specimen is serum 0.01–5 ml. Enzyme reaction proceeds at 37° C. for 5 minutes or more. Optimum pH of the enzyme is pH 7.5–9.0. The enzymatic reaction is carried out in the buffer of pH 7.5–9.0 containing amino acid or peptide as an acceptor such as glycylglycine to determine amine [2] which forms relative to γ-GTP activity. Examples of buffer are phosphate, borate, barbital, carbonate, triethanolamine, glycine or trishydroxymethylamino methane.

Quantitative determination of amine [2] can be made by teating with oxidase in the presence of coupler [3]. Coloring reaction is completed at optimum pH of oxidase, generally pH 6–7, to form chromogen by oxidative condensation. Examples of buffer used are phosphate, borate, carbonate, acetate or trishydroxymethylamino methane buffer. Enzymatic reaction proceeds at approximately 37° C. Chromogen formed by oxidative condensation of amine [2] and coupler [3] has absorption maxima at 550–750 nm depending upon the kind of coupler [3]. In general, the chromogen shows blue color having absorption maxima at 570–700 nm, with high sensitivity and stability without deviation by temperature, and is not affected by contaminant such as birilubin, and is preferable for LAP or γ-GTP assay.

In the present invention, an enzymatic reaction on amide compound [1] by LAP or γ-GTP and enzymatic oxidative condensation reaction by amine [2] and coupler [3] can be proceeded simultaneously. In that case, optimum pH should be a common pH for LAP or γ-GTP and oxidase such as pH 7.0. Buffer solution can be selected by the same as hereinbefore.

Quantitative determination of the thus formed chromogen can preferably be made colorimetrically at specific absorption wave length of the chromogen. Determination of the specific absorption wave length can be made by conventionally measuring an absorption spectrum of the chromogen, and is performed generally at 550–770 nm.

LAP or γ-GTP activity in a sample can be measured by determining an amount of consumed oxygen and is preferably made by oxygen electrode. Further, the oxidase hereinabove is immobilized by known immobilizing technique and the said immobilized enzyme is combined with electrode to set up enzyme electrode. Quick, simple and repeated assay can be performed by the said enzyme electrode, and teh said electrode can be assembled in automatic assay system. Also, the measurement by electrochemical changes on oxygen electrode can save an amount of expensive enzyme. LAP or γ-GTP activity can be determined by converting from the recorded or indicated amount of an electrochemical change measured by electrode.

As hereinabove explained, the present invention is simple assay method in each reaction step and is an exact and quick LAP or γ-GTP assay method. Moreover the chromogen formed has absorption maxima at 550–750 nm which cannot be affected by the contaminant in specimens.

Embodiment of peptidase assay using amide compound [4] is as follows.

Amide compound [4] or salt thereof is treated by peptidase in sample, especially LAP or γ-GTP, to liberate aniline derivative [5]. The said aniline derivative is converted to chromogen by the action of oxidizing agent or oxidase, and the coloring compound is colorimetrically measured, or amount of consumed oxygen is measured by oxidase.

An oxidative coloration is preferably a colorimetric assay of chromogen which is generated by oxidative condensation of coupler [3] and aniline derivative [5]. Examples of coupler are aromatic compound which forms chromogen which is oxidatively condensed with aniline derivative [5], and are preferably phenol, aminophenol, aniline or naphthol series compound of the coupler [3] hereinbefore.

The oxidative condensation is carried out at pH 4–12 to complete coloring reaction. Buffers or aqueous alkaline solution for controling the pH are carbonate, phosphate, borate buffer or alkaline hydroxide solution. The condensation proceeds in the presence of oxidizing agent or oxidase which can oxidatively condense the aniline derivative [5] with coupler [3]. Examples of oxidizing agent are generally halogen series oxidizing agent such as periodate, chloramine T or hypochlorous acid, peroxide series oxidizing agent such as persulfate or hydrogen peroxide, or cyanoferric complex, and preferable example is sodium metaperiodate. Prefarable examples of oxidase are laccase, ascorbate oxidase or tyrosinase. Oxidation by oxidase can be carried out as the same way as that of amide compound [1].

Chromogen thus formed by the oxidative condensation of aniline derivative [5] and coupler [3] has maximum absorption wave length approximately at 550–770 nm depending on the kind of coupler, and is generally colored pigment, having 570–680 nm. The said pigmentation is high sensitive and stable without affecting by temperature and contaminant in specimen such as bilirubin. Therefore it does no cause positive error, and so preferable for peptidase assay such as LAP or γ-GTP.

Another colorimetric assay method of aniline derivative [5] is colorimetry of the color which is produced by treating pentacyanoferric complex with peroxide. Examples of peroxide are sodium periodate, potassium periodate, potassium permanganate or hydrogen peroxide. Hydrogen peroxide is preferable. Stable ferric complex reagent can be obtained by mixing the above cyanoferric complex with bicarbonate such as sodium bicarbonate, lithium bicarbonate or potassium bicarbonate and low molecular dextran. The said complex mixture is stable in freeze dried powder and is preferable for a reagent of kit for colorimetric assay.

Colorimetric assay using cyanoferric complex is carried out at an acidic pH, preferably at pH 3–7, and most preferably pH 4–5.5. For maintaining Ph conventional buffer is used. Example of buffer is 0.01–1M, preferably 0.05–0.4M lactate, citrate or oxalate buffer.

Chromogen, which is formed by the reaction of cyanoferric complex and aniline derivative [5], has maximum absorption approximately at 700 nm with stable tone, and is suitable for assaying peptidase such as LAP or γ-GTP.

Further, assay of peptidase such as LAP or γ-GTP by colorimetry of chromogen, which is formed by the reaction of sodium pentacyanoacoferriate $Na_2[Fe(CN)_5.H_2O]$ and liberated aniline derivative [5], can be made. Furtheremore, the peptidase assay can be colorimetrically made by conventional chemical colorimetric assay method, for example colorimetry of aromatic amine, such as diazocoupling method, or colorimetry of Schiff base which is formed by reacting with aldehyde series compound.

LAP assay using amide compound [4] is illustrated in details as follows.

Synthetic substrate for LAP, L-leucyl-3,5-dihalogeno-4-hydroxyanilide is enzymatically reacted with LAP in sample to liberate aniline derivative [5], i.e. 3,5-dihalogeno-4-hydroxyaniline. Serum 0.01–5 ml as specimen is used, and the enzymatic reaction is carried out at 37° C. for over 5 minutes. Optimum pH of the reaction is pH 6.5–8.0, and is maintained with a buffer solution such as phosphate, barbital, borate or Trishydroxyaminomethane.

The thus formed aniline derivative [5] can be colorimetrically determined, in the presence of coupler such as p-xylenol and alkaline condition, the formed chromogen by oxidative condensation with oxidating reagent such as sodium metaperiodate, or alternatively, colorimetrically determined by using coloration reagent obtained by oxidation of pentacyanoaminoferroate with oxidating reagent such as hydrogen peroxide. Further, colorimetric assay can be made by treating with oxidase to consume oxygen and liberate chromogen, and measuring the consumed oxygen or formed chromogen.

Embodiment of γ-GTP assay using amide compound [4] is illustrated in details as follows.

Synthetic substrate for γ-GTP, γ-L-glutamyl-3,5-dihalogeno- 4-hydroxyanilide is enzymatically reacted with γ-GTP in sample to liberate aniline derivative [5] of 5-dihalogeno-4-hydroxyaniline. Amount of sample specimen is serum 0.01–5 ml.

Enzymatic reaction of γ-GTP is carried out at 37° C. for over 5 minutes at optimum pH of pH 7.5–9.0. Reaction can be carried out in a buffer of pH 7.5–9.0 containing amino acid or peptide, as an acceptor, such as glycylglycine, and aniline derivative [5], which is formed in proportion to γ-GTP activity, is determined. Examples of buffer solution are phosphate, barbital, borate, carbonate, triethanolamine, glycine or Tris(hydroxymethyl)aminomethane.

Determination of aniline derivative [5] can be made by the same way as of in an assay of LAP.

As explained hereinabove, an assay method of the present invention using synthetic substrate amide compound [4] is simple in each reaction step and so peptidase such as LAP or γ-GTP car be assayed rapidly and accurately. Furthermore, since the formed chromogen has maximum absorption at 550–750 nm, an affect of contaminant in specimen can be avoided, and hence the accurate assay of peptidase can be provide.

Further, an assay method of the present invention is carried out with mild enzymatic reaction step, moreover LAP or γ-GTP can be enzymatically assayed with simple single step reaction. The method can easily be set up for automatic system, and so rate assay, which has been impossible by conventional prior chemical assay method, can be possible.

Following examples illustrate the present invention but are not construed as limiting.

Following abbreviations are used.
Leu: L-leucyl;
γ-Glu: γ-L-glutamyl;
BOC: t-butyloxycarbonyl;
OSu: N-hydroxysuccinimide ester;
AcOH: acetic acid;
BuOH: butanol.

EXAMPLE 1

L-leucyl-3,5-dichloro-4-hydroxyanilide.HCl:

A solution (25 ml) of BOC-Leu-OSu (3.28 g, 10 mM) in dioxane was added dropwise with stirring at 0°–5° C. in 2,6-dichloro-4-aminophenol (1.78 g, 10 mM) and sodium bicarbonate (1.26 g, 15 mM) dissolved in water (25 ml). Mixture was stirred for overnight at room temperature and dioxane was distilled off in vacuo at below 30° C. Residue dissolved in ethyl acetate (200 ml) was washed three times with saturated sodium bicarbonate, water, 1 N-HCl and saturated NaCl solution (each 50 ml). Ethyl acetate layer was dried with anhydrous magnesium sulfate and concentrated in vacuo to obtain BOC-L-leucyl-3,5-dichloro-4-hydroxyanilide (2.96 g). The product dissolved in 2 N-HCl/AcOH (15 ml) was stirred at room temperature and crystallized by adding dry diethyl ether (100 ml) which was subjected to twice decantation with dry ether. Crystals were dried in vacuo to obtain L-leucyl-3,5-dichloro-4-hydroxyanilide.HCl.

Yield: 1.89 g (yield: 57.7%)
Mol. formula: $C_{12}H_{16}N_2O_2Cl_2.HCl$
m.p.: 127°–133° C. (decomp.)
TLC: Rf=0.63 [BuOH-AcOH-water (4:1:1)]
IR spectrum (KBr): FIG. 1.

EXAMPLE 2

L-leucyl-3,5-dibromo-4-hydroxyanilide.HCl:

A solution (70 ml) of BOC-Leu-OSu (6.01 g, 18.3 mM) in dioxane was added dropwise at 0°–5° C. in 2,6-dibromo-4-aminophenol (4.90 g, 18.8 mM) and sodium bicarbonate (1.68 g, 20 mM) dissolved in water (20 ml). Mixture was stirred at room temperature for overnight and dioxane was distilled off at below 30° C. Residue dissolved in ethyl acetate (400 ml) and washed three times with satureated aqueous sodium bicarbonate, water, 1 N-HCl and saturated NaCl solution (each 100 ml). Ethyl acetate layer was dried with anhydrous magnesium sulfate and concentrated in vacuo to obtain BOC-L-leucyl-3,5-dibromo-4-hydroxyanilide (5.8 g). The product dissolved in 2 N-HCl/AcOH (3.0 ml) was stirred at room temperature for 2 hours, then dry ether was added therein to crystallize the product L-leucyl-3,5-dibromo-4-hydroxyanilide.HCl.

Yield: 2.50 g (yield: 32.8%)
Mol. formula: $C_{12}H_{16}N_2O_2BR_2HCL$ (416.54)
TLC (silica-gel): Rf=0.65 [BuOH:AcOH:water (4:1:1)]
m.p.: 131°–134° C. (decomp.)
IR spectrum (KBr): FIG. 2.

EXAMPLE 3

γ-L-glutamyl-3,5-dichloro-4-hydroxyanilide:

N.N-phthaloyl-L-glutamic acid anhydride (5.16 g, 20 mM) and 4-amino-2,6-dichlorophenol (3.56 g, 20 mM) dissolved in dioxane (50 ml) was stirred at 60° C. for 2 hours. Dioxane was distilled off in vacuo and hydrazine hydrate (1.5 ml) in methanol (50 ml) was added therein, then allow to stand at room temperature for 2 days. Methanol was distilled off in vacuo, added water to the residue and adjusted to pH 3 by adding 0.5 N-HCl to obtaine precipitated γ-L-glutamyl-3.5-dichloro-4-hydroxyanilide (3.96 g).

Yield: 3.96 g yield 64.5%)
Mol. formula: $C_{11}H_{12}N_2O_4Cl_2$
m.p.: 214°–217° C. (decomp.)
silica-gel TLC: Rf=0.49 (BuOH-AcOH-H$_2$O (4:1:1)
IR spectrum (KBr): FIG. 3

EXAMPLE 4

γ-L-glutamyl-3,5-dibromo-4-hydroxyanilide:
N,N-phthaloyl-L-glutamic acid anhydride (2.18 g, 8.4 mM) and 4-amino-2,6-dibromophenol (2.26 g, 8.4 mM) dissolved in dioxane (20 ml) was stirred at 60° C. for 1.5 hour. Dioxane was distilled off in vacuo, and hydroazine hydrate (0.7 ml) in methanol (20 ml) was added to the residue, then allowed to stand at room temp. for 2 days. Methanol was distilled off in vacuo, added water to the residue and adjusted to pH 3 by adding 0.5 N-HCl to obtain precipitated γ-L-glutamyl-3,5-dibromo-4-hydroxyanilide (2.13 g).
Yield: 2.13 g (yield: 64.0%)
Mol. formula: $C_{11}H_{12}N_2O_4Br_2$
m.p.: 191°–194° C. (decomp.) [199°–200° C. (decomp.) measured by method for m.p. according to Pharmacopoeia Japonica] (decomp.)
silica-gel TLC: Rf=0.53 (BuOH-AcOH-H$_2$O=4:1:1)
IR spectrum (KBr): FIG. 4.

EXAMPLE 5

LAP assay using L-leucyl-4-N,N-diethylaminoanilide, 1-naphthol-2-sulfonic acid and laccase:
Substrate solution containing 0.1M phosphate buffer solution (pH 7.0) of L-leucyl-4-N,N-diethylaminoanilide.2HCl (2 mM) and coupler potassium 1-naphthol-2-sulfonate (0.5 mM) was prepared. Laccase solution (100 μl, 330 U) obtained from *Poryporus versicolor* and serum (LAP: 879 G-R units/ml, 50 μl) were added to the substrate solution (2.0 ml) and incubated at 37° C. to form pigment. (The absorption spectrum of pigment is shown in FIG. 5, absorption maximum at 655 nm). In the reaction, absorption at 655 nm of the formed pigment was continuously measured at each time. Result is shown in FIG. 6.
FIG. 7 is shown the result obtained by using serum of 414 G-R units/ml.
As shown in FIGS. 6 and 7, serum LAP activity can be exactly measured by an assay method of the present invention, and contrary to the prior known chemical colorimetry, reaction mixture is colored simultanelusly with starting LAP action, hence rate assay can be possible.

EXAMPLE 6

LAP assay using L-leucyl-4-N,N-diethylaminoanilide, phenol and laccase:
Substrate containing L-leucyl-4-N,N-diethylaminoanilide.2HCl (2 mM) and coupler phenol (1 mM) in 0.1M phosphate buffer (pH 7.0) was prepared. Laccase solution (100 μl, 330 U) and serum (50 μl, LAP: 879 G-R units/ml) were added to the substrate solution (2 ml) and incubated at 37° C. to form pigment. In the reaction, color (maximum absorption at 670 nm) formed each reaction time was continuously measured at 670 nm. Result is shown in FIG. 8.
As shown in FIG. 8, an assay method of the present invention is simple and exact assay method for LAP, meoreover reaction mixture became colored simultaneously with starting LAP action, in which rate assay can be possible.

Absorption curve of the pigment formed by the above process at each wave length is shown in FIG. 9, wherein the maximum absorption is at 670 nm.

EXAMPLE 7

LAP assay using L-leucyl-4-N,N-diethylaminoanilide, coupler (2,3-dimethylphenol, 2,4-dimethylphenol, 2,5-dimethylphenol and 2m6-dimethylphenol) and laccase:
In example 5, 1-naphthol-2-sulfonate was replaced by 2,3-dimethylphenol, 2,4-dimethylphenol, 2,5-dimethylphenol or 2,6-dimethylphenol to prepare substrate solution containing L-leucyl-4-N,N-diethylaminoanilide.2HCl (2 mM) and coupler (0.5 mM) in 0.1M phosphate buffer (pH 7.0). Laccase solution (100 μl, 330 U) and serum (50 μl, LAP: 879 G-R units/ml) were added to the substrate solution (2 ml) and incubated at 37° C. After 10 minutes, absorption of pigment formed was measured at maximum absorption wave length thereof. Result is shown in Table 1.

TABLE 1

| Coupler | maximum absorption | Optical Density |
|---|---|---|
| 2.3-dimethylphenol | 630 nm | 0.168 |
| 2,4-dimethylphenol | 630 nm | 0.187 |
| 2,5-dimethylphenol | 650 nm | 0.231 |
| 2,6-dimethylphenol | 630 nm | 0.193 |

EXAMPLE 8

LAP assay using L-leucyl-4-N,N-diethylaminoaniline, coupler (1-naphthol-2-sulfonate, phenol, 2,3-dimethylphenol, 2,4-dimethylphenol, 2,5-dimethylphenol or 2,6-dimethylphenol) and ascorbate oxidase:
Substrate solution containing L-leucyl-4-N,N-diethylaminoaniline.2HCl (2 mM) and coupler (potassium 1-naphthol-2-sulfonate, phenol, 2,3-dimethylphenol, 2,4-dimethylphenol, 2,5-dimethylphenol or 2,6-dimethylphenol) in 0.1M phosphate buffer (pH 7.0) was prepared. Ascorbate oxidase obtained from chayote (*Sechium edule*) solution (100 μl, 130 U) and serum (50 μl, LAP: 879 G-R units/ml) were added and incubated at 37° C. After 10 minutes, absorption of pigment formed was measured at maximum absorption wave length thereof. Result is shown in Table 2.

TABLE 2

| Coupler | maximum absorption | Optical Density (OD) |
|---|---|---|
| 1-naphtol-2-sulfonate | 655 nm | 0.411 |
| phenol | 670 nm | 0.347 |
| 2,3-dimethylphenol | 630 nm | 0.356 |
| 2,4-dimethylphenol | 630 nm | 0.267 |
| 2,5-dimethylphenol | 650 nm | 0.222 |
| 2,6-dimethylphenol | 630 nm | 0.427 |

EXAMPLE 9

LAP assay using L-leucyl-4-N,N-dimethylaminoanilide, 1-naphthol-2-sulfonate and laccase:
In example 5, L-leucyl-4-N,N-diethylaminoanilide.2HCl was replaced by L-leucyl-4-N,N-dimethylaminoanilide.2HCl and serum (LAP: 879 G-R units/ml) was added, and the remaining procedure was carried out as same as in example 5.
Maximum absorption of the pigment formed was 650 nm, and absorption ratio of each reaction time was measured at 650 nm. Result is shown in FIG. 10.

As shown in FIG. 10, LAP activity can be assayed by the method of the present invention.

EXAMPLE 10

LAP assay using L-leucyl-4-N,N-dimethylaminoanilide, phenol and laccase:

In example 6, L-leucyl-4-N,N-diethylaminoanilide.2HCl was replaced by L-leucyl-4-N,N-dimethylaminoanilide.2HCl and operation was performed as same as in example 6. Maximum absorption wave length of the pigment formed was at 655 nm. Absorption ratio at each reaction time is shown in FIG. 11. As shown in FIG. 11, LAP assay of the present invention is excellent.

EXAMPLE 11

LAP assay using L-leucyl-3,5-dibromo-4-hydroxyanilide, 1-naphthol-2-sulfonate and ascorbate oxidase:

Substrate solution containing L-leucyl-3.5-dibromo-4-hydroxyanilide.HCl (2 mM) and potassium 1-naphthol-2-sulfonate (0.5 mM) in 0.1M phosphate buffer (pH 7.0) was prepared. A solution (20 μl) containing ascorbate oxidase (130 U) and arylamidase (Boehringer, 1000 G-R units/ml) was added to the substrate solution (2 ml) and incubated at 37° C. At each reaction time, absorption of the formed pigment was measured at 630 nm. Result is shown in FIG. 12. As shown in FIG. 12, the assay method of the present invention provides excellent LAP assay, and rate assay can be possible because of simultaneous coloring with starting the LAP reaction. Absorption curve of the pigment is shown in FIG. 13.

EXAMPLE 12

LAP assay using L-leucyl-3,5-dibromo-4-hydroxyanilide, 1-naphthol-2-sulfonate, ascorbate oxidase or laccase:

Substrate solution (1.0 ml) prepared by the same as in example 11 was added in the reaction cell (inner volume: 1 ml) assembled with oxygen electrode and preheated to 37° C. A solution (100 μl) containing ascorbate oxidase (350 U) and arylamidase (1000 G-R units/ml) was added thereto and incubated at 37° C. Amount of consumed oxygen at each time was measured by oxygen electrode. Result is shown in FIG. 14, in which assay can advantageously be made by oxygen electrode.

In the same experiment, ascorbate oxidase was replaced by laccase (250 U), in which excellent result was obtained as shown in FIG. 15.

EXAMPLE 13

LAP assay using L-leucyl-3,5-dibromo-4-hydroxyanilide, coupler (phenol, 2,5-dimethylphenol) and laccase:

In example 11, 1-naphthol-2-sulfonate was replaced by phenol (0.5 mM) or 2.5-dimethylphenol (0.5 mM) to prepare substrate solution. A solution (20 μl) containing laccase (330 U) and arylamidise (1000 G-R units/ml) was added to the substrate solution (2 ml), and incubated at 37° C. for 10 minutes. Absorption ratio of the formed pigment was measured by maximum absorption wave length. Result is shown in Table 3.

TABLE 3

| Coupler | maximum absorption wave length | Optical Density (OD) |
|---|---|---|
| phenol | 610 nm | 0.160 |
| 2,5-dimethylphenol | 585 nm | 0.452 |

EXAMPLE 14

LAP assay using L-leucyl-3.5-dibromo-4-hydroxyanilide, phenol and tyrosinase:

Substrate solution containing L-leucyl-3,5-dibromo-4-hydroxyanilide.HCl (2.5 mM) and phenol (0.5 mM) in 0.1M phosphate buffer (pH 7.0) was prepared. Tyrosinase solution (100 μl, 300 U) and arylamidase (1000 G-R units/ml, 20 μl) were added in substrate solution (2 ml) and incubated at 37° C. for 10 minutes.

Absorption ratio of the formed pigment was measured at its maximum absorption wave length at 610 nm. ($OD_{610}$=0.158). LAP can be assayed with good result.

EXAMPLE 15

LAP assay using L-leucyl-2-methyl-4-aminoanilide, 1-naphthol-2-sulfonate and laccase:

Substrate solution containing L-leucyl-2-methyl-4-aminoanilide.2HCl (2 mM) and potassium 1-naphthol-2-sulfonate (0.5 mM) in phosphate buffer (pH 7.0) was prepared.

Laccase solution (100 μl, 330 U) and arylamidase solution (50 μl, 1000 G-R units/ml) were added to substrate solution (2 ml) and incubated at 37° C. for 30 minutes. Absorption ratio of the formed pigment was measured at its maximum absorption wave length at 565 nm ($OD_{565}$=0.143).

EXAMPLE 16

LAP assay using L-leucyl-4-aminoanilide, 1-naphthol-2-sulfonate and laccase:

Substrate solution containing L-leucyl-4-aminoanilide.2HCl(2.5 mM) and potassium 1-naphthol-2-sulfonate (0.5 mM) in 0.1M phosphate buffer (pH 7.0) was prepared.

Laccase solution (100 μl, 330 U) and arylamidase solution (50 μl, 1000 G-R units/ml) were added to substrate solution (2 ml) and incubated at 37° C. for 30 minutes. Absorption ratio of the formed pigment was measured at its maximum absorption wave length at 565 nm($OD_{565}$=0.143).

EXAMPLE 17

LAP assay using L-leucyl-4-N,N-dipropylanilide, 1-naphthol-2-sulfonic acid and laccase:

Substrate solution containing L-leucyl-4-N,N-dipropylaminoanilide.2HCl (2 mM) and potassium p-naphthol-2-sulfonate (0.5 mM) in 0.1M phosphate buffer (pH 7.0) was prepared. Laccase solution (100 μl, 330 U) and arylamidase solution (50 μl, 1000 G-R units/ml) were added to the substrate solution (2 ml), and incubated at 37° C. for 10 minutes. Absorption ratio of the formed pigment was measured at maximum absorption wave length at 650 nm ($OD_{650}$=0.430).

EXAMPLE 18

LAP assay using L-leucyl-3.5-dichloro-4-hydroxyanilide, 1-naphthol-2-sulfonate or phenol and laccase:

Substrate solution containing L-leucyl-3,5-dichloro-4-hydroxyanilide.HCl (2 mM) and potassium 1-naphthol-2-sulfonate (0.5 mM) in 0.1M phosphate buffer (pH 7.0). Laccase solution (100 μl, 330 U) and arylamidase solution (20 μl, 1000 G-R units/ml) were added to the substrate solution (2 ml) and incubated at 37° C. for 10 minutes. Absorption ratio of the formed pigment was measured at 630 nm. ($OD_{630}=0.535$).

The above 1-naphthol-2-sulfonate was replaced by 0.5 mM phenol and measured the formed pigment at 610 nm. ($OD_{610}=0.111$).

EXAMPLE 19

LAP assay using L-leucyl-4-N-ethyl-N-hydroxyethylaminoanilide, 2,6-dibromophenol and laccase:

Laccase (100 μl, 330 U) and arylamidase solution (20 μl, 1000 G-R units/ml) were added to the substrate solution (2 ml) containing L-leucyl-4-N-ethyl-N-hydroxyethylaminoanilide.2HCl (2 mM) and 2,6-dibromophenol (0.5 mM) in 0.1M phosphate buffer (pH 7.0), and incubated at 37° C. for 5 minutes. Absorption ratio of the formed pigment was measured at 705 nm. ($OD_{705}=1.47$).

EXAMPLE 20

LAP assay using L-leucyl-anilide, 3,5-dibromo-4-hydroxyaniline and laccase:

In example 19, L-leucyl.HCl-4-N-ethyl-N-hydroxyethylaminoanilide.2HCl was replaced by L-leucyl-anilide.HCl (2 mM). Absorption ratio of the formed pigment was measured at its maximum absorption wave length at 655 nm. ($OD_{655}=0.178$).

EXAMPLE 21

LAP assay using L-leucyl-2-ethylanilide, 3,5-dibromo-4-hydroxyaniline and laccase:

In example 19, L-leucyl-4-N-ethyl-N-hydroxyethylaminoanilide.2HCl was replaced by L-leucyl-2-ethylanilide.HCl (2 mM). Absorption ratio of the formed pigment was measured at its maximum absorption wave length at 675 nm. ($OD_{675}=0.428$).

EXAMPLE 22

LAP assay using L-leucyl-2-carboxyanilide, 3,5-dibromo-4-hydroxyaniline or 4-N,N-diethylaminoaniline and laccase:

Laccase solution (100 μl, 330 U) and arylamidase solution (50 μl, 1000 G-R units/ml) were added to the substrate solution containing L-leucyl-2-carboxyanilide.HCl (2 mM) and 3,5-dibromo-4 hydroxyaniline (0.5 mM) in 0.1M phosphate buffer (pH 7.0), and incubated at 37° C. for 10 minutes. Absorption ratio of the formed pigment was measured at its maximum absorption wave length at 645 nm. ($OD_{645}=0.397$).

In the above, 3,5-dibromo-4-hydroxyaniline was replaced by 4-N,N-diethylaminoaniline.2HCl (0.5 mM). Absorption ratio of the formed pigment was measured by its maximum absorption wave length at 690 nm. ($OD_{690}=0.613$).

EXAMPLE 23

LAP assay using various synthetic substrate, coupler and laccase:
Synthetic substrate for LAP assay:
(A) L-leucyl-3,5-dibromo-4-hydroxyanilide.HCl;
(B) L-leucyl-4-N,N-diethylaminoanilide.2HCl; or
(C) L-leucyl-4-N,N-dimethylaminoanilide.2HCl.
Coupler:
(1) N-ethyl-N-hydroxyethylaniline;
(2) 2,6-dibromophenol;
(3) 2,4-dichlorophenol;
(4) 2,6-dimethocyphenol;
(5) aniline;
(6) m-toluidine;
(7) anthranilic acid;
(8) m-methylphenol;
(9) o-carboxymethylphenol;
(10) N-ethyl-N-hydroxyethyl-m-toluidine;
(11) N,N-dimethyl-m-toluidine;
(12) o-ethylaniline;
(13) α-naphthol;
(14) N,N-dimethylaniline;
(15) N,N-diethylaniline;
(16) o-chlorophenol;
(17) m-chlorophenol;
(18) m-ethylphenol;
(19) o-methoxyphenol;
(20) 4-chloro-m-phenylenediamine;
(21) 2-methyl-6-chlorophenol;
(22) 2-chloro-5-methylphenol;
(23) 4-chloro-1-naphthol;
(24) 1-naphthol-2-carboxylic acid.

Substrate solution containing synthetic substrate (2 mM) and coupler (0.5 mM) in 0.1M phosphate buffer (pH 7.0) were prepared. Laccase solution (100 μl, 330 U) and arylamidase (50 μl, 1000 G-R units/ml) were added to the substrate solution (2 ml), and incubated at 37° C. for 10 minutes. Absorption ratio of the formed pigment was measured at its maximum absorption wave length. Result is shown in Table 4.

TABLE 4

| Coupler | Synthetic substrate for LAP | | |
|---|---|---|---|
| | (A) | (B) | (C) |
| (1) | $OD_{705} = 3.712$ | $OD_{730} = 1.849$ | |
| (2) | $OD_{670} = 1.031$ | $OD_{705} = 0.187$ | $OD_{700} = 0.168$ |
| (3) | $OD_{660} = 0.508$ | $OD_{695} = 0.259$ | |
| (4) | $OD_{580} = 0.567$ | $OD_{635} = 0.157$ | |
| (5) | $OD_{655} = 0.45$ | $OD_{690} = 0.301$ | $OD_{690} = 0.271$ |
| (6) | $OD_{675} = 0.396$ | $OD_{710} = 0.260$ | $OD_{700} = 0.234$ |
| (7) | $OD_{645} = 0.401$ | $OD_{690} = 0.244$ | $OD_{690} = 0.219$ |
| (8) | $OD_{600} = 0.495$ | $OD_{665} = 0.201$ | |
| (9) | $OD_{590} = 0.693$ | $OD_{650} = 0.329$ | |
| (10) | $OD_{715} = 0.421$ | $OD_{745} = 3.79$ | |
| (11) | | $OD_{740} = 3.54$ | |
| (12) | $OD_{675} = 1.08$ | $OD_{700} = 2.05$ | |
| (13) | $OD_{575} = 0.338$ | $OD_{640} = 0.157$ | |
| (14) | $OD_{700} = 0.261$ | $OD_{730} = 1.01$ | $OD_{725} = 0.907$ |
| (15) | $OD_{705} = 0.536$ | $OD_{730} = 1.22$ | |
| (16) | $OD_{650} = 0.698$ | $OD_{690} = 0.449$ | $OD_{680} = 0.404$ |
| (17) | $OD_{650} = 0.495$ | | $OD_{685} = 0.203$ |
| (18) | $OD_{605} = 0.338$ | | |
| (19) | $OD_{590} = 0.468$ | | |
| (20) | $OD_{630} = 0.842$ | | |
| (21) | $OD_{610} = 0.63$ | | |
| (22) | $OD_{635} = 0.567$ | | |
| (23) | $OD_{580} = 0.356$ | | $OD_{640} = 0.05$ |
| (24) | $OD_{590} = 0.419$ | | |

EXAMPLE 24

γ-GTP assay using γ-L-glutamyl-4-N,N-diethylaminoanilide, 1-naphthol-2-sulfonate and laccase:

Substate solution containing γ-L-glutamyl-4-N,N-diethylaminonilide (5 mM), glycylglycine (100 mM) and potassium 1-naphthol-2-sulfonate (0.5 mM) in 50 mM phosphate buffer (pH 8.0) was prepared. Laccase (100 μl, 1000 U/ml) and serum (50 μl, γ-GTP: 416 mU/ml) were added to the substrate solution (2 ml), and incubated at 37° C. Absorption ratio of the formed pigment was measured at each reaction time at 655 nm. Result is shown in FIG. 16. Serum (γ-GTP: 105 mU/ml) was measured and the result is shown in FIG. 17. As shown in FIG. 16 and 17, γ-GTP activity can be excellently assayed by the method of the present invention, and reaction mixture is colored simultaneously with starting γ-GTP action and so rate assay can be possible. Absorption curve of the formed pigment is shown in FIG. 18.

EXAMPLE 25

Y-GTP assay using γ-L-glutamyl-4-N,N-diethylaminoanilide, 1-naphthol-2-sulfonate and laccase:

Substrate solution (1 ml) in example 24 was added in reaction cell (inner volume 1 ml) set with oxygen electrode and pre-heated at 37° C. A solution (100 μl) containing laccase (200 U) and serum (γ-GTP: 416 mU/ml) was added thereto, then incubated at 37° C. Amount of consumed oxygen was measured by oxygen electrode. Oxygen consumed rate is shown in FIG. 19, in which showing γ-GTP activity can advantageously be measured.

EXAMPLE 26

γ-GTP assay using γ-L-glutamyl-4-N,N-diethylaminoanilide, 1-naphthol-2-sulfonate and ascorbate oxidase:

Substrate solution (2 ml) was prepared by the same way as in example 24. Ascorbate oxidase solution (100 μl, 100 U) and serum (50 μl, γ-GTP: 416 mU/ml) were added thereto and incubated at 37° C. for 5 minutes and 10 minutes, respectively. Absorption ratio of the formed pigment was measured in each time at 655 nm (maximum absorption wave length). Optical density at 655 nm at 5 minutes reaction is $OD_{655}=0.949$, and at 10 minutes is $OD_{655}=1.895$.

EXAMPLE 27

γ-GTP assay using γ-L-glutamyl-3,5-dichloro-4-hydroxyanilide, lpnaphthol-2-sulfonate and laccase or tyrosinase:

Substrate solution containing γ-L-glutamyl-3,5-dichloro-4-hydroxyanilide (5 mM), glycylglycine (100 mM) and potassium 1-naphthol-2-sulfonate (0.5 mM) in 50 mM borate buffer (pH 7.1) was prepared. Laccase solution (100 μl, 100 U) and serum (50 μl, γ-GTP: 416 mU/ml) were added to the substrate solution (2 ml), and incubated at 37° C. for 10 minutes. Absorption ratio of the formed pigment was measured at its maximum absorption wave length at 630 nm. ($OD_{630}=1.044$).

Laccase was replaced by tyrosinase solution (100 μl, 100 U) in the above experiment, and conducted the same way as above. Result was $OD_{630}=1.042$.

EXAMPLE 28

γ-GTP assay using various synthetic substrate for γ-GTP and coupler and ascorbate oxidase:

Synthetic substrate:
  (A) γ-L-glutamyl-4-N,N-diethylaminoanilide;
  (B) γ-L-glutamyl-4-N,N-dimethylaminoanilide;
  (C) γ-L-glutamyl-4-N,N-dipropylaminoanilide;
  (D) γ-L-glutamyl-3,5-dibromo-4-hydroxyanilide.

Coupler:
  (1) potassium 1-naphthol-2-sulfonate;
  (2) 2.5-dimethylphenol;
  (3) 2,6-dibromophenol;
  (4) 2,6-dimethoxyphenol;
  (5) N,N-diethylaniline;
  (6) N-ethyl-N-hydroxyethylaniline;
  (7) N,N-dimethyl-m-toluidine;
  (8) o-ethylaniline;
  (9) m-chlorophenol;
  (10) o-methylphenol;
  (11) o-methoxyphenol;
  (12) α-naphthol;
  (13) phenol.

Substrate solution containing substrate (5 mM), glycylglycine (100 mM) and coupler (0.5 mM) in 50 mM borate buffer (pH 8.0) was prepared. Ascorbate oxidase solution (100 μl, 100 U) and serum (50 μl, γ-GTP: 416 mU/ml) were added to the substrate solution (2 ml), and incubated at 37° C. for 5 minutes. Absorption ratio of the formed pigment was measured at maximum absorption wave length thereof. Result is shown in Table 5.

TABLE 5

| Coupler | Synthetic substrate | | | |
|---|---|---|---|---|
|  | (A) | (B) | (C) | (D) |
| (1) |  | $OD_{650} = 0.978$ | $OD_{650} = 0.902$ | $OD_{630} = 0.803$ |
| (2) |  |  |  | $OD_{585} = 0.645$ |
| (3) | $OD_{705} = 0.368$ | $OD_{700} = 0.379$ |  | $OD_{670} = 1.120$ |
| (4) | $OD_{635} = 0.313$ | $OD_{595} = 0.322$ |  | $OD_{580} = 0.511$ |
| (5) | $OD_{730} = 1.362$ | $OD_{725} = 1.404$ |  |  |
| (6) | $OD_{730} = 1.627$ |  |  | $OD_{705} = 1.907$ |
| (7) | $OD_{740} = 2.426$ |  |  |  |
| (8) | $OD_{700} = 1.871$ |  |  | $OD_{675} = 0.826$ |
| (9) | $OD_{695} = 0.453$ |  |  | $OD_{655} = 0.495$ |
| (10) | $OD_{650} = 0.331$ |  |  | $OD_{590} = 0.622$ |
| (11) |  |  |  | $OD_{590} = 0.605$ |
| (12) | $OD_{640} = 0.297$ |  |  |  |
| (13) |  | $OD_{655} = 0.562$ |  | $OD_{610} = 0.717$ |

EXAMPLE 29

LAP assay using L-leucyl-3,5-dichloro-4-hydroxyanilide, and sodium metaperiodate - p-xylenol:

Substrate solution containing L-leucyl-3,5-dichloro-4-hydroxynilide.HCl (5 mM) dissolved in 0.1M phosphate buffer (pH 7.0) was prepared. Serum specimen obtained from patient (20 μl, LAP: 236 G-R units) was added to the substrate solution (1 ml), mixed well and incubated at 37° C. for 20 minutes. Oxidizing reagent solution (3 ml) containing sodium metaperiodate (2 mM) and p-xylenol (10 mM) in 0.2 N-KOH was added to develop color. Absorption ratio of the formed color was measured at 585 nm to obtain $OD_{585}=0.18$.

EXAMPLE 30

LAP assay using L-leucyl-3,5-dibromo-4-hydroxyanilide, and sodium-metaperiodate.- p-xylenol:

Substrate solution containing L-leucyl-3,5-dibromo-4-hydroxyanilide.HCl (5 mM) dissolved in 0.1M phosphate buffer (pH 7.0) was prepared. Serum specimen obtained from patient (20 μl, LAP: 250 G-R units) was added to the substrate solution (1 ml), mixed well and incubated at 37° C. for 20 minutes. Oxidizing reagent solution (3 ml) containing sodium metaperiodate (2 mM) and p-xylenol (10 mM) in 0.2 N-KOH was added to develop color.

Absorption ratio of the color was measured at 585 nm. ($OD_{585}$=0.18).

EXAMPLE 31

γ-GTP assay using γ-L-glutamyl-3,5-dichloro-4-hydroxyanilide and sodium metaperiodate-p-xylenol:

Substrate solution containing γ-L-glutamyl-3,5-dichloro-4-hydroxyanilide glycylalycine (100 mM) (5 mM) and glycylglycine (5 mM) in 5 mM Tris-HCl buffer (pH 8.0) was prepared. Serum specimen (10 μl, γ-GTP: 130 mU/ml) was added to the substrate solution (0.5 ml), mixed well and incubated at 37° C. for 20 minutes. Oxidizing reagent solution (2 ml) containing sodium metaperiodate (2 mM) and p-xylenol (10 mM ) in 0.2 N-KOH was added to develop color. Absorption ratio was measured at 585 nm. ($OD_{585}$=0.112).

EXAMPLE 32

γ-GTP assay using γ-L-glutamyl-3,5-dibromo-4-hydroxyanilide and sodium metaperiodate, - p-xylenol:

Substrate solution containing γ-L-glutamyl-3,5-dibromo-4-hydroxyanilide (5 mM) and glycylglycine (100 mM dissolved in 50 mM Tris-HCl buffer (pH 8.0). Patient's serum specimen (10 μl, γ-GTP: 130 mU/ml) was added to the substrate solution (0.5 ml) and incubated at 37° C. for 20 minutes. Oxidizing reagent solution (2 ml) containing sodium metaperiodate (2 mM) and p-xylenol (10 mM) in 0.2 N-KOH was added to develop color. Absorption ratio was measured at 585 nm ($OD_{585}$=0.140).

EXAMPLE 33

LAP assay using L-leucyl-3,5-dibromo-4-hydroxyanilide, and sodium metaperiodate, 2-chloro-5-methylphenol:

Substrate solution (5 mM) containing L-leucyl-3,5-dibromo-4-hydroxyanilide.HCl dissolved in 0.1M phosphate buffer (pH 7.0) was prepared. Patient's serum specimen (20 μl, LAP: 250 G-R units) was added to the substrate solution (1 ml) and incubated at 37° C. for 20 minutes. Oxidizing reagent solution (3 ml) containing sodium metaperiodate (2 mM) and 2-chloro-5-methylphenol (5 mM) in 0.2 N-KOH was added to develop color. Absorption ratio of the color at 635 nm was measured. ($OD_{635}$=0.33).

EXAMPLE 34

γ-GTP assay using γ-L-glutamyl-3,5-dibromo-4-hydroxyanilide, sodium metaperiodate, 2-chloro-5-methylphenol:

Substrate solution containing γ-L-glutamyl-3,5-dibromo-4 -hydroxyanilide (5 mM) and glycylglycine (100 mM) dissolved in 50 mM Tris-HCl buffer (pH 8.0) was prepared. Patient's serum specimen (10 μl, γ-GTP: 130 mU/ml) was added to the substrate solution (0.5 ml) and incubated at 37° C. for 20 minutes. Oxidizing reagent (2 ml) containing sodium metaperiodate (2 mM) and 2-chloro-5-methylphenol (5 mM) in 0.2 N-KOH was added to develop color. Absorption ratio at 635 nm was measured to obtain $OD_{635}$=0.214.

EXAMPLE 35

LAP assay using L-leucyl-3,5-dibromo-4-hydroxyanilide and sodium pentacyanoaminoferroate:

0.3% hydrogen peroxide (60 ml) was added to sodium pentacyanoaminoferroate (2 g) dissolved in water (20 ml), and further 10% sodium bicarbonate solution (20 ml) was added. Dextran T-10 (Pharmacia, 4 g) was added therein to prepare color developer undiluted solution. Reaction stopper-color developer undiluted solution was prepared by adding 0.2M citrate buffer (50 ml, pH 4.5) containing 1% NaCl and 0.5% Tween 80 to the color developer undiluted solution (1 ml).

Serum specimen obtained from patient (20 μl, LAP: 250 G-R units) was added to L-leucyl-3,5-dibromo-4-hydroxyanilide.HCl (5 mM) dissolved in 0.1M phosphate buffer (pH 7.0)(1 ml), mixed well and incubated at 37° C. for 20 minutes. Reaction stopper-color developer solution (5 ml) was added and allowed to stand at room temperature for 20 minutes to develop color. Asorption ratio for 700 nm was measured to obtain $OD_{700}$=0.21.

EXAMPLE 36

γ-GTP assay using γ-L-glutamyl-3,5-dibromo-4-hydroxyanilide and sodium pentacyano aminoferroate:

Patient's serum specimen (20 μl, γ-GTP: 130 mU/ml) was added to a solution (1 ml) dissolved γ-L-glutamyl-3,5-dibromo-4-hydroxyanilide (5 mM) and glycylglycine (100 mM) in 50 mM Tris-HCl buffer (pH 8.0), mixed well and incubated at 37° C. for 20 minutes. Reaction was stopped and developed as same as in example 35 to obtain the absorption ratio of $OD_{700}$=0.132.

EXAMPLE 37

LAP assay using L-leucyl-3,5-dibromo-4-hydroxyanilide and sodium pentacyanoacoferriate:

Substrate solution (5 mM) containing L-leucyl-3,5-dibromo-4-hydroxyanilide.HCl dissolved in 0.1M phosphate buffer (pH 7.0) was prepared. Patient's serum specimen (20 μl, LAP: 250 G-R units) was added to the substrate solution (1 ml), mixed well and incubated at 37° C. for 15 minutes. A solution (4 ml), prepared by adding 0.2M EDTA.2Na solution (pH 11, 90 ml) in 1% sodium pentacaynoacoferriate (30 ml), was added thereto and incubated at 37° C. for 15 minutes. Absorption ratio was measured at 730 nm to obtain $OD_{730}$=0.232.

1% sodium pentacyanoacoferriate was prepared by uv-irradiation for 15 minutes to a solution of 1% sodium nitroprusside Na[Fe(CN)$_5$NO]-1% sodium carbonate.

EXAMPLE 38

Standard curve of γ-GTP using γ-L-glutamyl-3,5-dibromo-4-hydroxyanilide:

Substrate solution containing γ-L-glutamyl-3,5-dibromo-4-hydroxynilide (5 mM) and glycylglycine (100 mM) in 50 mM Tris-HCl buffer (pH 8.0) was prepared. Serum γ-GTP (74–370 mU/ml, 10 μl ) was added to the substrate solution (0.5 ml), mixed well and incubated at 37° C. for 20 minutes. Oxidizing reagent solution containing sodium metaperiodate (2 mM) and p-xylenol (10 mM) in 0.2 N-KOH was added to develop color. Absorption ratio of the formed color was measured at 585 nm. Result is shown in FIG. 20 in which serum γ-GTP can be measured advantageously.

EXAMPLE 39

LAP assay using L-leucyl-3.5-dichloro-4-hydroxyanilide or L-leucyl-3,5-dibromo-4-hydroxyanilide, 2,5-dimethylphenol and ascorbate oxidase:

Substrate solution containing L-leucyl-3.5-dichloro-4-hydroxyanilide.HCl (2 mM) or L-leucyl-3,5-dibromo-4-hydroxyanilide. HCl (2 mM) and 2,5-dimethylphenol (2 mM) in 0.1M phosphate buffer (pH 7.0) was prepared. Ascorbate oxidase (130 U) and patient's serum psecimen (20 μl, LAP: 1113 G-R units/ml) were added to the substrate solution (2 ml) and incubated at 37° C. for 10 minutes. Absorption ration was measured at its maximum absorption wave length. Results are:

L-leucyl-3,5-dibhloro-4-hydroxyanilide: $OD_{585}=0.586$

L-leucyl-3,5-dibromo-4-hydroxyanilide: $OD_{585}=0.756$

EXAMPLE 40

LAP assay using L-leucyl-3.5-dichloro-4-hydroxyanilide, 2,5-dimethylphenol and laccase:

Substrate solution containing L-leucyl-3.5-dichloro-4-hydroxyanilide.HCl (2 mM) and 2,5-dimethylphenol (2 mM) in 0.1M phosphate buffer (pH 7.0) was prepared. A solution (20 μl) containing laccase (330 U) and arylamidase (1000 G-R units/ml) was added to the substrate solution (2 ml) and incubated at 37° C. for 10 minutes. Absorption ratio at 585 nm was $OD_{585}=0.386$.

EXAMPLE 41

γ-GTP assay using γ-L-glutamyl-3,5-dichloro-4-hydroxyanilide, 2,5-dimethylphenol and ascorbate oxidase:

Substrate solution containing γ-L-glutamyl-3,5-dichloro-4-hydroxyanilide (5 mM), glycylglycine (100 mM) and 2,5-dimethylphenol (0.5 mM) in 50 mM borate buffer (pH 8.0) was prepared. Ascorbate oxidase (100 μl, 100 U) and serum (50 μl, γ-GTP: 416 mU/ml) were added to the substrate solution (2 ml) and incubated at 37° C. for 5 minutes. Absorption ratio at 585 nm was $OD_{585}=0.547$.

EXAMPLE 42

γ-GTP assay using γ-L-glutamyl-3,5-dichloro-4-hydroxyanilide or γ-L-glutamyl-3,5-dibromo-4-hydroxyanilide, 2,5-dimethylphenol and laccase:

Substrate solution containing γ-L-glutamyl-3,5-dichloro-4-hydroxyanilide (5 mM) or γ-L-glutamyl-3,5-dibromo-4-hydroxyanilide (5 mM), glycylglycine (100 mM) and 2,5-dimethylphenol (0.5 mM) in 50 mM borate buffer (pH 8.0) was prepared. Laccase solution (100 μl, 100 U) and serum (50 μl, γ-GTP: 416 mU/ml) were added to each substrate solution (2 ml), and incubated at 37° C. for 5 minutes. Absorption ratio of the formed color was measured. Results are:

γ-L-glutamyl-3,5-dichloro-4-hydroxyanilide: $OD_{585}=0.476$

γ-L-glutamyl-3,5-dibromo-4-hydroxyanilide: $OD_{585}=0.526$

Figure 1:
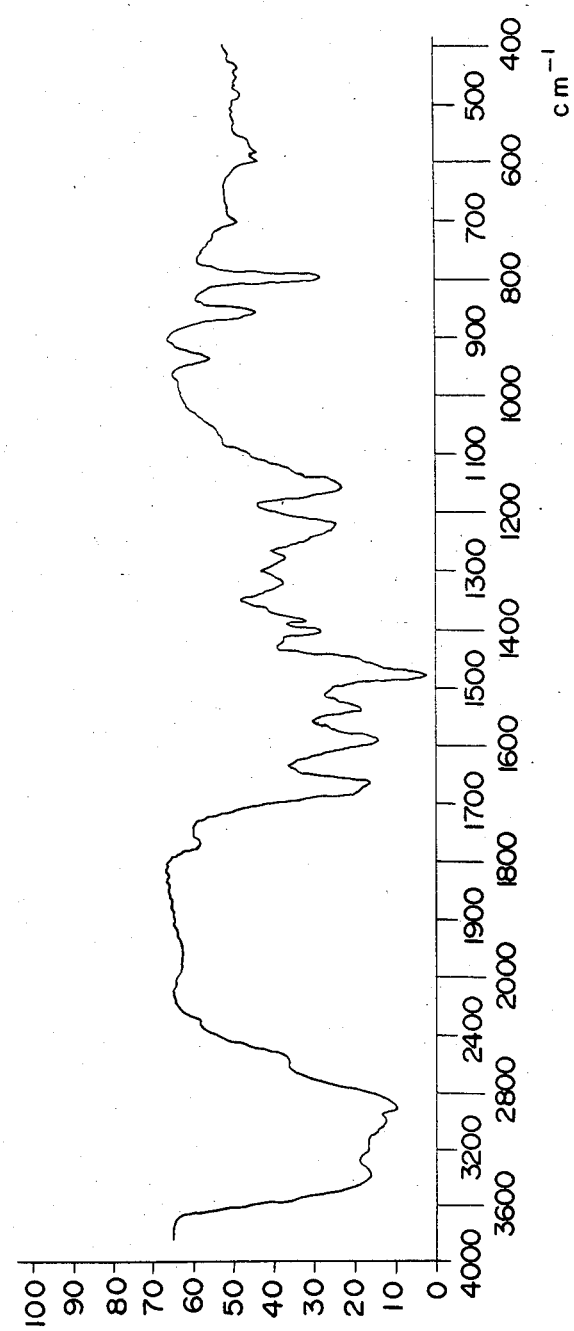
FIG. 1: IR spectrum of L-leucyl-3,5-dichloro-4-hydroxyanilide.HCl.
Figure 2:
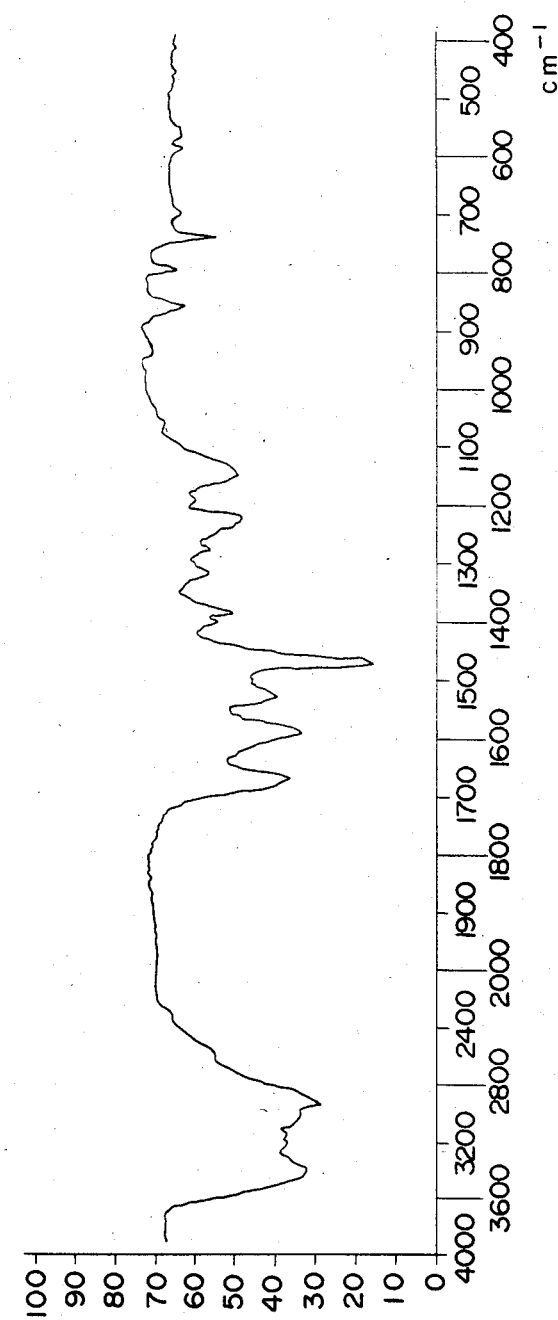
FIG. 2: IR spectrum of BOC-L-leucyl-3,5-dibromo-4-hydroxyanilide.
Figure 3:
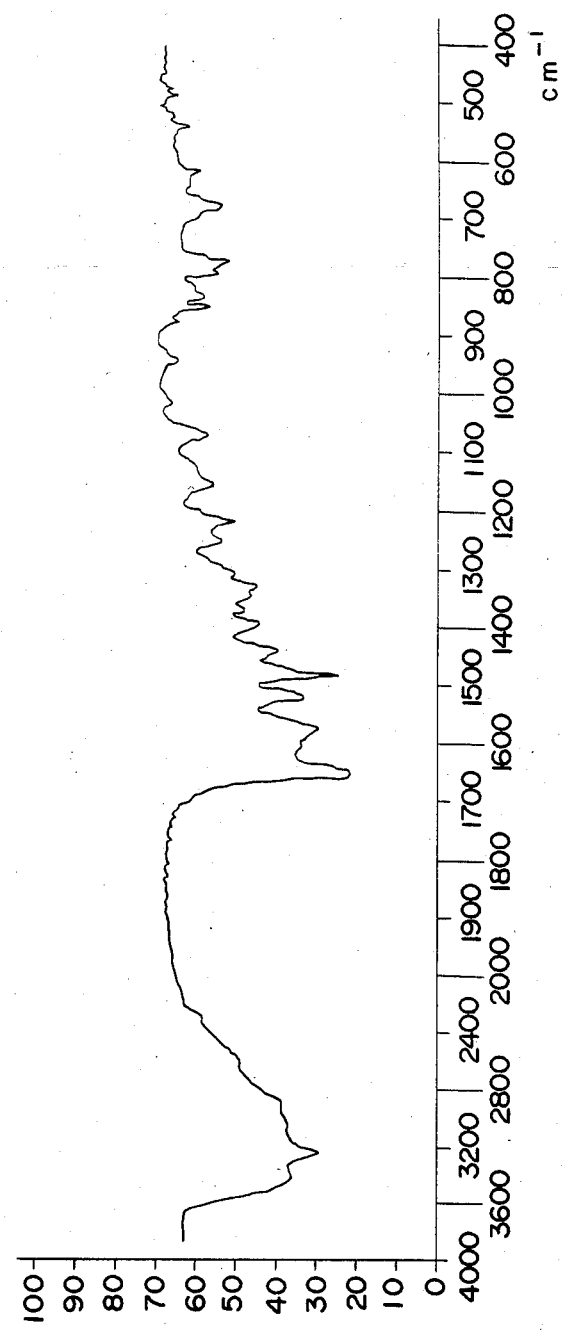
FIG. 3: IR spectrum of γ-L-glutamyl-3,5-dichloro-4-hydroxyanilide.
Figure 4:
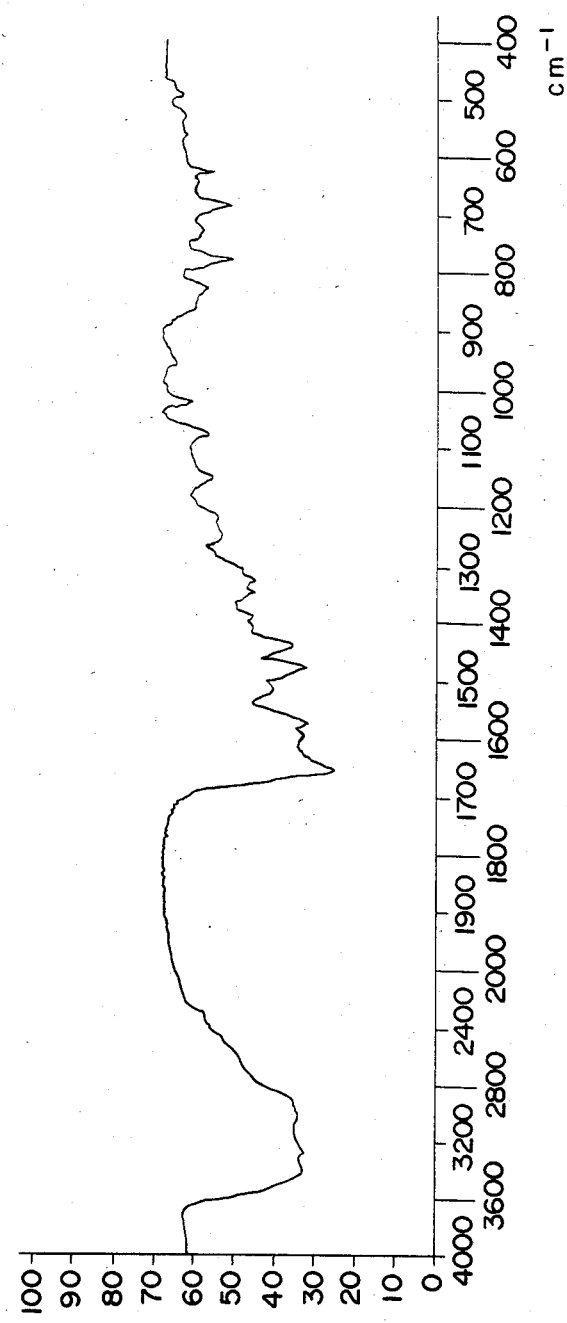
FIG. 4: IR spectrum of γ-L-glutamyl-3,5-dibromo-4-hydroxyanilide.
Figure 5:
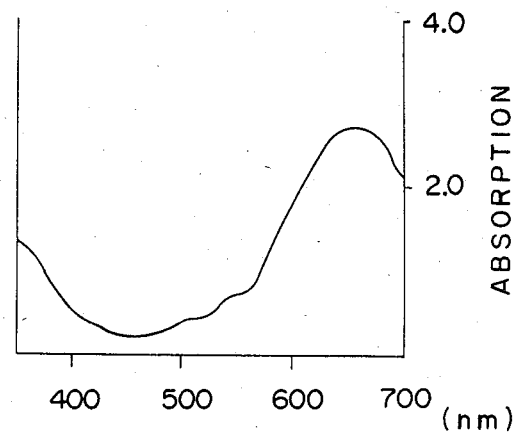
FIG. 5: Absorption curve of pigment formed by L-leucyl-4-N,N-diethylaminoanilide, 1-naphthol-2-sulfonate, laccase and serum.
Figure 6:
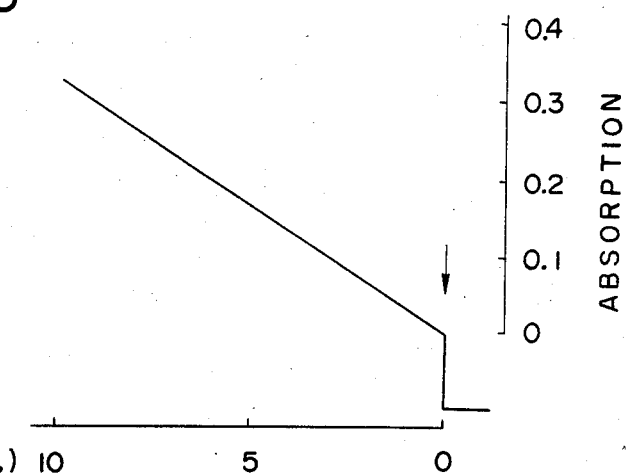
FIGS. 6 and 7: Curve of absorption ratio change by measuring continuous increasing absorption ratio on reaction time using L-leucyl-4-N,N-diethylaminoanilide, 1-naphthol-2-sulfonate, laccase and serum.
Figure 7:
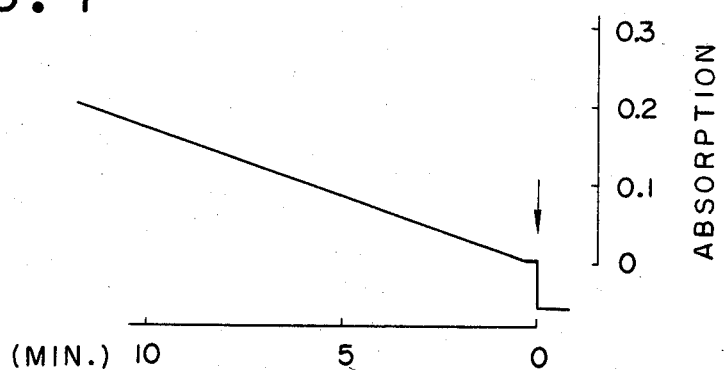
Figure 8:
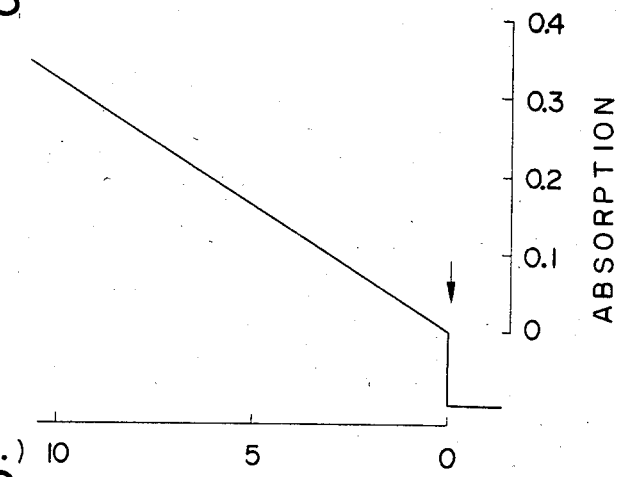
FIG. 8: Curve of absorption ratio change as the same as in FIGS. 6 and 7, except 1-naphthol-2-sulfonate is replaced ny phenol.
Figure 9:
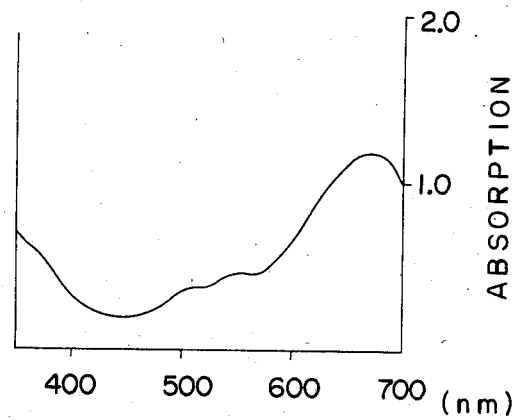
FIG. 9: Absorption curve of the pigment formed in the condition as the same as in FIG. 8.
Figure 10:
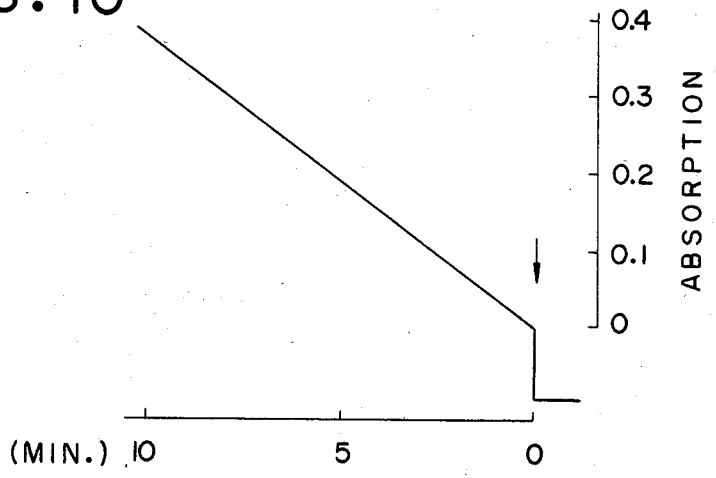
FIG. 10: Curve of absorption ratio change as the same as in FIGS. 6 and 7, except L-leucyl-4-N,N-diethylaminoanilide is replaced by L-leucyl-4-N,N-dimethylaminoanilide.
Figure 11:
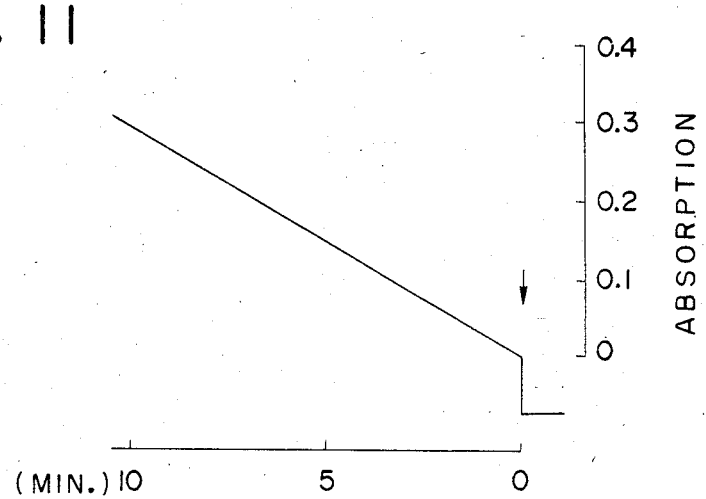
FIG. 11: Curve of absorption ratio change as the same as in FIG. 10, except 1-naphthol-2-sulfonate is replaced by phenol.
Figure 12:
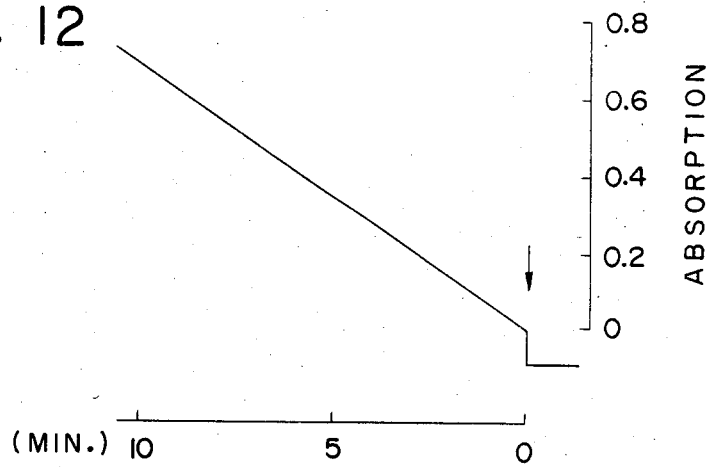
FIG. 12: Curve of absorption ratio change as the same as in FIGS. 6 and 7, except L-leucyl-4-N,N-diethylaminoanilide, laccase, and serum are replaced by L-leucyl-3,5-dibromo-4-hydroxyanilide, ascorbate oxidase and arylamidase.
Figure 13:
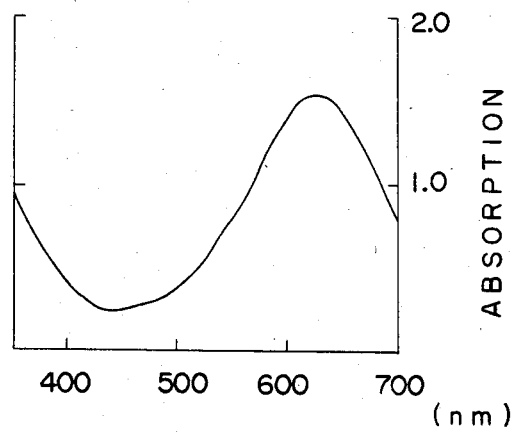
FIG. 13: Absorption curve of the formed pigment in the condition of the same in FIG. 12.
Figure 14:
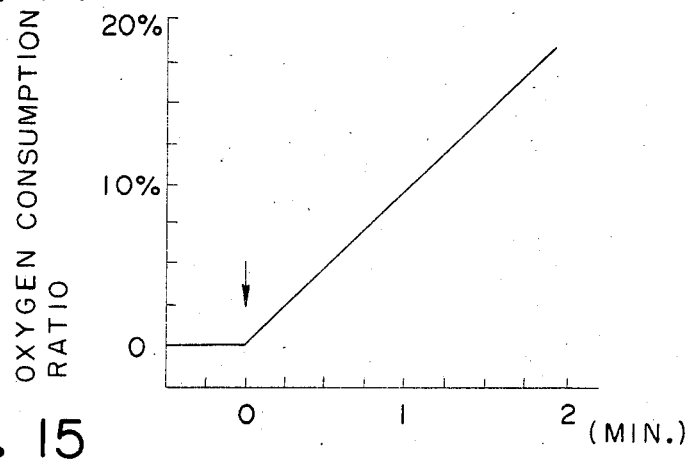
FIG. 14: Curve of oxygen consumption ratio on reaction time for the reaction using L-leucyl-3.5-dibromo-4-hydroxyanilide, 1-naphthol-2-sulfonate, ascorbate oxidase and arylamidase.
Figure 15:
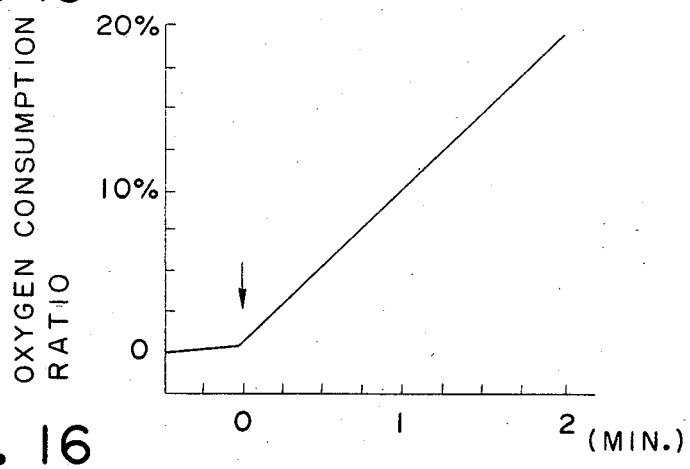
FIG. 15: Curve of oxygen consumption ratio on reaction time for the reaction using L-leucyl-3,5-dibromo-4-hydroxyanilide, 1-naphthol-2-sulfonate, laccase and arylamidase.
Figure 16:
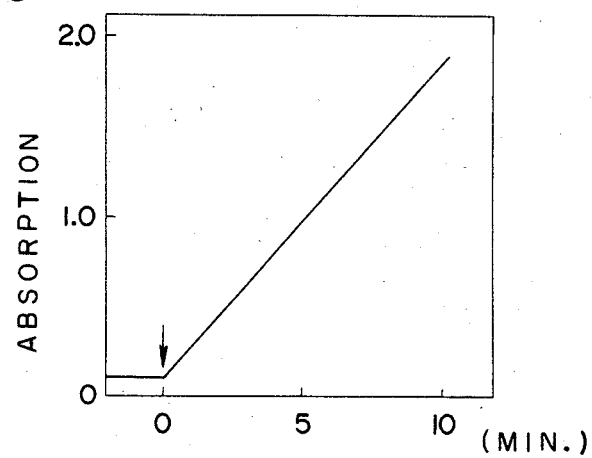
FIGS. 16 and 17: Curve of absorption ratio change by continuous measuring the increase of absorption ratio on the reaction time for the reaction using γ-L-glutamyl-4-N,N-diethylaminoanilide, glycylglycine, 1-naphthol-2-sulfonate, laccase and serum.
Figure 17:
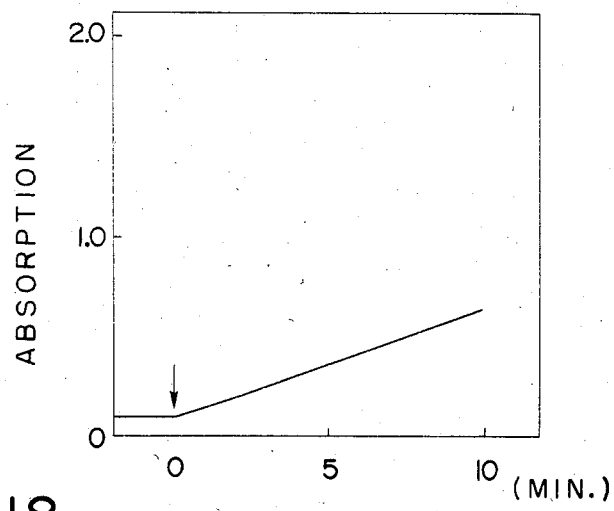
Figure 18:
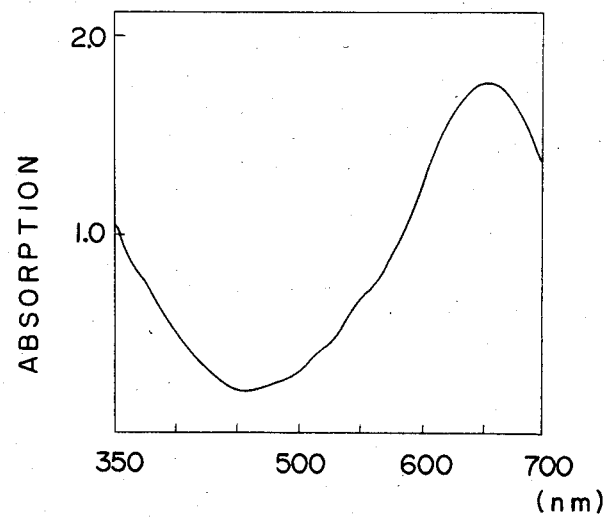
FIG. 18: Absorption curve of the formed pigment in the condition of the same in FIGS. 16 and 17.
Figure 19:
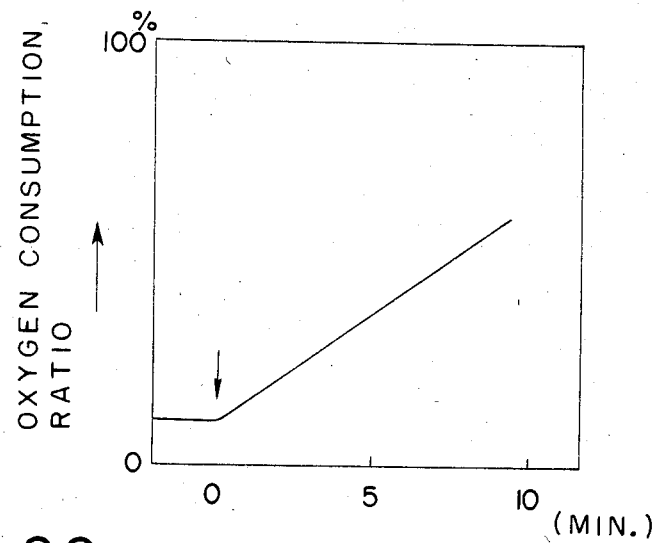
FIG. 19: Curve of oxygen consumption on reaction time for the reaction using γ-L-glutamyl-4-N,N-diethylaminoanilide, glycylglycine, 1-naphthol-2-sulfonate, laccase and serum.
Figure 20:
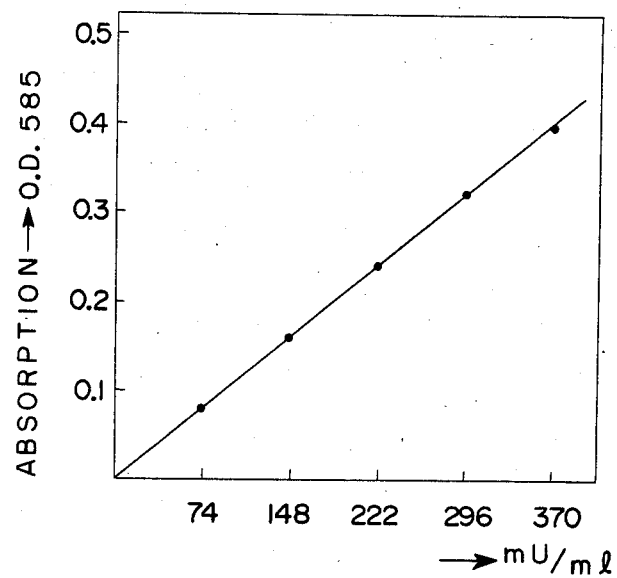
FIG. 20: Standard curve of γ-GTP using γ-L-glutamyl-3,5-dibromo-4-hydroxyanilide, glycylglycine, p-xylenol and sodium metaperiodate.

We claim:

1. A compound of the formula

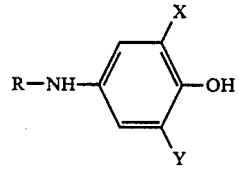

wherein R is L-leucyl or γ-L-glutamyl and X and Y are halogen and are the same or different, or a salt thereof.

2. A compound or salt thereof according to claim 1 wherein R is L-leucyl and said halogen is bromine or chlorine.

3. A compound or salt thereof according to claim 2 which is L-leucyl-3,5-dibromo-4-hydroxyanilide.

4. A compound of salt thereof according to claim 2 which is L-leucyl-3,5-dichloro-4-hydroxyanilide.

5. A compound or salt thereof according to claim 1 wherein R is γ-L-glutamyl and said halogen is bromine or chlorine.

6. A compound or salt thereof according to claim 5 which is γ-L-glutamyl-3,5-dibromo-4-hydroxyanilide.

7. A compound or salt thereof according to claim 5 which is γ-L-glutamyl-3,5-dichloro-4-hydroxyanilide.

* * * * *